United States Patent
Simaan et al.

(10) Patent No.: US 9,687,303 B2
(45) Date of Patent: Jun. 27, 2017

(54) DEXTEROUS WRISTS FOR SURGICAL INTERVENTION

(71) Applicant: Vanderbilt University, Nashville, TN (US)

(72) Inventors: Nabil Simaan, Nashville, TN (US); Roger E. Goldman, New York, NY (US); Andrea Bajo, Fort Lauderdale, FL (US)

(73) Assignee: Vanderbilt University, Nashville, TN (US)

( * ) Notice: Subject to any disclaimer, the term of this patent is extended or adjusted under 35 U.S.C. 154(b) by 218 days.

(21) Appl. No.: 14/391,659

(22) PCT Filed: Apr. 19, 2013

(86) PCT No.: PCT/US2013/037336
§ 371 (c)(1),
(2) Date: Oct. 9, 2014

(87) PCT Pub. No.: WO2013/158974
PCT Pub. Date: Oct. 24, 2013

(65) Prior Publication Data
US 2015/0073434 A1 Mar. 12, 2015

Related U.S. Application Data

(60) Provisional application No. 61/636,001, filed on Apr. 20, 2012.

(51) Int. Cl.
*A61B 34/30* (2016.01)
*A61B 19/00* (2006.01)
*A61B 34/00* (2016.01)

(52) U.S. Cl.
CPC .......... *A61B 19/2203* (2013.01); *A61B 34/30* (2016.02); *A61B 34/71* (2016.02); *A61B 2034/305* (2016.02)

(58) Field of Classification Search
CPC ......... A61B 31/30; A61B 31/71; A61B 31/70; A61B 31/37; A61B 31/72; A61B 31/32;
(Continued)

(56) References Cited

U.S. PATENT DOCUMENTS

| 2,988,237 A | 6/1961 | Devol, Jr. |
| 3,580,099 A | 5/1971 | Mosher |

(Continued)

FOREIGN PATENT DOCUMENTS

| EP | 2335558 | 6/2011 |
| WO | 2005009482 | 2/2005 |

(Continued)

OTHER PUBLICATIONS

A. Bajo, and N. Simaan, Kinematics-Based Detection and Localization of Contacts Along Multisegment Continuum Robots. IEEE Transactions on Robotics 28, 2 (Apr. 2012), 291-302.

(Continued)

*Primary Examiner* — Jocelin Tanner
(74) *Attorney, Agent, or Firm* — Michael Best & Friedrich LLP

(57) ABSTRACT

A rotatable wrist connecting a gripper tool to the distal end of a continuum robot shaft. The rotatable wrist includes a wrist hub that is non-rotatably connected to the distal end of the shaft. A wrist capstan is rotatably connected to the wrist hub and non-rotatably connected to the gripper. A flexible wire loop extends through the wrist hub and partially contacts the wrist capstan. Linear movement of the flexible wire loop through the shaft of the continuum robot causes rotation of the wrist capstan due to friction between the flexible wire loop and the wrist capstan. The wrist also supports selective detachability and control of roll, pitch and roll, pitch yaw and roll according to different embodiments.

18 Claims, 7 Drawing Sheets

(58) Field of Classification Search
CPC .............. A61B 31/35; A61B 2034/305; A61B 2034/306; A61B 2034/301; A61B 2034/302
See application file for complete search history.

(56) References Cited

U.S. PATENT DOCUMENTS

| | | | |
|---|---|---|---|
| 4,744,264 A | 5/1988 | Milenkovic | |
| 4,795,296 A | 1/1989 | Jau | |
| 4,802,461 A | 2/1989 | Cho | |
| 5,046,375 A | 9/1991 | Salisbury, Jr. et al. | |
| 5,231,989 A | 8/1993 | Middleman et al. | |
| 5,337,732 A | 8/1994 | Grundfest et al. | |
| 5,345,937 A | 9/1994 | Middleman et al. | |
| 5,386,741 A | 2/1995 | Rennex | |
| 5,397,323 A | 3/1995 | Taylor et al. | |
| 5,410,638 A | 4/1995 | Colgate et al. | |
| 5,480,406 A | 1/1996 | Nolan et al. | |
| 5,662,587 A | 9/1997 | Grundfest et al. | |
| 5,749,828 A | 5/1998 | Solomon et al. | |
| 6,113,593 A | 9/2000 | Tu et al. | |
| 6,197,017 B1 | 3/2001 | Brock et al. | |
| 6,309,346 B1 | 10/2001 | Farhadi | |
| 6,554,844 B2 | 4/2003 | Lee et al. | |
| 6,669,711 B1 | 12/2003 | Noda | |
| 6,676,684 B1 | 1/2004 | Morley et al. | |
| 6,692,485 B1 | 2/2004 | Brock et al. | |
| 6,817,974 B2 | 11/2004 | Cooper et al. | |
| 6,837,892 B2 | 1/2005 | Shoham | |
| 6,843,793 B2 | 1/2005 | Brock et al. | |
| 6,858,005 B2 | 2/2005 | Ohline et al. | |
| 6,860,878 B2 | 3/2005 | Brock | |
| 6,949,106 B2 | 9/2005 | Brock et al. | |
| 7,021,173 B2 | 4/2006 | Stoianovici et al. | |
| 7,099,745 B2 | 8/2006 | Ebert | |
| 7,214,230 B2 | 5/2007 | Brock et al. | |
| 7,235,089 B1 | 6/2007 | McGuckin, Jr. | |
| 7,316,681 B2 | 1/2008 | Madhani et al. | |
| 7,391,173 B2 | 6/2008 | Schena | |
| 7,682,319 B2 | 3/2010 | Martin et al. | |
| 7,699,835 B2 | 4/2010 | Lee et al. | |
| 7,787,681 B2 | 8/2010 | Zhang et al. | |
| 7,822,249 B2 | 10/2010 | Garty et al. | |
| 7,837,615 B2 | 11/2010 | Le et al. | |
| 7,854,738 B2 | 12/2010 | Lee et al. | |
| 7,887,549 B2 | 2/2011 | Wenderow et al. | |
| 7,959,557 B2 | 6/2011 | Weitzner et al. | |
| 8,025,635 B2 | 9/2011 | Eaton et al. | |
| 8,088,101 B2 | 1/2012 | Chang et al. | |
| 8,114,062 B2 | 2/2012 | Muni et al. | |
| 8,116,886 B2 | 2/2012 | Simaan et al. | |
| 8,172,828 B2 | 5/2012 | Chang et al. | |
| 8,303,576 B2 | 11/2012 | Brock | |
| 8,311,626 B2 | 11/2012 | Hlavka et al. | |
| 8,337,521 B2 | 12/2012 | Cooper et al. | |
| 8,343,141 B2 | 1/2013 | Madhani et al. | |
| 8,365,633 B2 | 2/2013 | Simaan et al. | |
| 8,372,019 B2 | 2/2013 | Goldenberg et al. | |
| 8,377,077 B2 | 2/2013 | Reis | |
| 8,409,234 B2 | 4/2013 | Stahler et al. | |
| 8,414,505 B1 | 4/2013 | Weitzner | |
| 8,414,598 B2 | 4/2013 | Brock et al. | |
| 8,444,549 B2 | 5/2013 | Viola et al. | |
| 8,460,236 B2 | 6/2013 | Roelle et al. | |
| 8,480,618 B2 | 7/2013 | Wenderow et al. | |
| 8,486,053 B2 | 7/2013 | Niemeyer | |
| 8,498,691 B2 | 7/2013 | Moll et al. | |
| 8,504,201 B2 | 8/2013 | Moll et al. | |
| 8,545,551 B2 | 10/2013 | Loulmet | |
| 8,551,115 B2 | 10/2013 | Steger et al. | |
| 8,585,731 B2 | 11/2013 | Abbate et al. | |
| 8,864,757 B2 | 10/2014 | Klimovitch et al. | |
| 2002/0120252 A1 | 8/2002 | Brock et al. | |
| 2003/0120305 A1 | 6/2003 | Jud et al. | |
| 2003/0135204 A1* | 7/2003 | Lee | A61B 34/20 606/1 |
| 2004/0116906 A1 | 6/2004 | Lipow | |
| 2004/0176751 A1 | 9/2004 | Weitzner et al. | |
| 2005/0043718 A1 | 2/2005 | Madhani et al. | |
| 2005/0054900 A1 | 3/2005 | Mawn et al. | |
| 2005/0059960 A1 | 3/2005 | Simaan et al. | |
| 2005/0228440 A1 | 10/2005 | Brock et al. | |
| 2006/0036182 A1 | 2/2006 | Daniels et al. | |
| 2006/0047302 A1 | 3/2006 | Ortiz et al. | |
| 2006/0058861 A1 | 3/2006 | Gibson et al. | |
| 2006/0156851 A1 | 7/2006 | Jacobsen et al. | |
| 2006/0241414 A1 | 10/2006 | Nowlin et al. | |
| 2006/0258938 A1 | 11/2006 | Hoffman et al. | |
| 2007/0197939 A1 | 8/2007 | Wallace et al. | |
| 2007/0225787 A1 | 9/2007 | Simaan et al. | |
| 2008/0009838 A1* | 1/2008 | Schena | A61B 34/71 606/1 |
| 2008/0033240 A1 | 2/2008 | Hoffman et al. | |
| 2008/0065108 A1 | 3/2008 | Diolaiti | |
| 2008/0071288 A1 | 3/2008 | Larkin et al. | |
| 2008/0114492 A1 | 5/2008 | Miegel et al. | |
| 2008/0179301 A1 | 7/2008 | Garty et al. | |
| 2008/0181473 A1 | 7/2008 | Garty et al. | |
| 2008/0188800 A1 | 8/2008 | Bencini et al. | |
| 2008/0243063 A1 | 10/2008 | Camarillo | |
| 2008/0243064 A1 | 10/2008 | Stahler et al. | |
| 2008/0243106 A1 | 10/2008 | Coe et al. | |
| 2008/0245173 A1 | 10/2008 | Schwerin et al. | |
| 2008/0249536 A1 | 10/2008 | Stahler et al. | |
| 2008/0262513 A1 | 10/2008 | Stahler et al. | |
| 2008/0302200 A1 | 12/2008 | Tobey | |
| 2009/0054222 A1 | 2/2009 | Zhang et al. | |
| 2009/0076476 A1 | 3/2009 | Barbagli et al. | |
| 2009/0076521 A1 | 3/2009 | Hansen | |
| 2009/0088774 A1 | 4/2009 | Swarup et al. | |
| 2009/0171151 A1 | 7/2009 | Choset et al. | |
| 2009/0216083 A1 | 8/2009 | Durant et al. | |
| 2009/0275818 A1 | 11/2009 | Rau et al. | |
| 2009/0275857 A1 | 11/2009 | Cabiri et al. | |
| 2010/0010504 A1 | 1/2010 | Simaan et al. | |
| 2010/0011900 A1 | 1/2010 | Burbank | |
| 2010/0030377 A1 | 2/2010 | Unsworth | |
| 2010/0069719 A1 | 3/2010 | Wehrheim | |
| 2010/0076269 A1 | 3/2010 | Makower et al. | |
| 2010/0079308 A1 | 4/2010 | Fabre et al. | |
| 2010/0099951 A1 | 4/2010 | Laby et al. | |
| 2010/0125165 A1 | 5/2010 | Troii et al. | |
| 2010/0152899 A1 | 6/2010 | Chang et al. | |
| 2010/0210391 A1* | 8/2010 | Dinger | B64C 13/28 475/149 |
| 2010/0256558 A1 | 10/2010 | Olson et al. | |
| 2010/0331857 A1* | 12/2010 | Doyle | A61B 34/30 606/130 |
| 2010/0331858 A1 | 12/2010 | Simaan et al. | |
| 2011/0015649 A1 | 1/2011 | Anvari et al. | |
| 2011/0066160 A1 | 3/2011 | Simaan et al. | |
| 2011/0071541 A1 | 3/2011 | Prisco et al. | |
| 2011/0071544 A1 | 3/2011 | Steger et al. | |
| 2011/0125165 A1 | 5/2011 | Simaan et al. | |
| 2011/0184241 A1 | 7/2011 | Zubiagte et al. | |
| 2011/0196419 A1 | 8/2011 | Cooper | |
| 2011/0213346 A1 | 9/2011 | Morley et al. | |
| 2011/0230894 A1 | 9/2011 | Simaan et al. | |
| 2011/0306929 A1 | 12/2011 | Levesque et al. | |
| 2011/0313243 A1 | 12/2011 | Zubiate et al. | |
| 2011/0319910 A1 | 12/2011 | Roelle et al. | |
| 2012/0071822 A1 | 3/2012 | Romo et al. | |
| 2012/0109274 A1 | 5/2012 | Simaan et al. | |
| 2012/0123395 A1 | 5/2012 | Stoy et al. | |
| 2012/0241576 A1 | 9/2012 | Yu | |
| 2012/0253131 A1 | 10/2012 | Malkowski et al. | |
| 2012/0289946 A1 | 11/2012 | Steger | |
| 2013/0012928 A1 | 1/2013 | Cooper et al. | |
| 2013/0023859 A1 | 1/2013 | Malkowski | |
| 2013/0090763 A1 | 4/2013 | Simaan et al. | |
| 2013/0096540 A1 | 4/2013 | Cooper et al. | |
| 2013/0110131 A1 | 5/2013 | Madhani et al. | |
| 2013/0131868 A1 | 5/2013 | Rucker et al. | |

(56) References Cited

U.S. PATENT DOCUMENTS

| | | | |
|---|---|---|---|
| 2013/0165869 A1 | 6/2013 | Blumenkranz et al. | |
| 2013/0165945 A9 | 6/2013 | Roelle et al. | |
| 2013/0178838 A1 | 7/2013 | Malkowski | |
| 2013/0190741 A1 | 7/2013 | Moll et al. | |
| 2013/0197539 A1 | 8/2013 | Simaan et al. | |
| 2013/0218141 A1 | 8/2013 | Hinman et al. | |
| 2013/0231529 A1 | 9/2013 | John et al. | |
| 2013/0269109 A1 | 10/2013 | Yu | |
| 2013/0274715 A1 | 10/2013 | Chan et al. | |
| 2013/0289581 A1 | 10/2013 | Yeung et al. | |
| 2013/0300537 A1 | 11/2013 | Bajo et al. | |
| 2013/0303945 A1 | 11/2013 | Blumenkranz et al. | |
| 2013/0306112 A1 | 11/2013 | Blumenkranz | |
| 2013/0338433 A1 | 12/2013 | Goldman et al. | |
| 2014/0058406 A1 | 2/2014 | Tsekos | |
| 2014/0330432 A1 | 11/2014 | Simaan et al. | |

FOREIGN PATENT DOCUMENTS

| | | | |
|---|---|---|---|
| WO | 2005112834 | 12/2005 | |
| WO | 2008036304 | 3/2008 | |
| WO | 2009094670 | 7/2009 | |
| WO | 2009097461 | 8/2009 | |
| WO | 2009097539 | 8/2009 | |
| WO | 2009124287 | 10/2009 | |
| WO | 2009140688 | 11/2009 | |
| WO | 2010042611 | 4/2010 | |
| WO | WO2010042611 A1 * | 4/2010 | ............ A61B 19/00 |
| WO | 2011063511 | 6/2011 | |
| WO | 2012015816 | 2/2012 | |
| WO | 2012049623 A1 | 4/2012 | |
| WO | 2013043804 | 3/2013 | |
| WO | 2013158974 | 10/2013 | |
| WO | 2013158978 | 10/2013 | |
| WO | 2013158983 | 10/2013 | |
| WO | 2013166293 | 11/2013 | |

OTHER PUBLICATIONS

R.E. Goldman, A. Bajo, and N. Simaan, Compliant Motion Control for Continuum Robots with Intrinsic Actuation Sensing. In 2011 IEEE International Conference on Robotics and Automation (Shanghai, China, 2011), pp. 1126-1132.
Bajo, A., Dharamsi, L., Netterville, J. L., Garrett, G. C., and Simaan, N (2013). Robotic-Assisted Micro-Surgery of the Throat: the Trans-Nasal Approach. In Accepted for publication in IEEE International Conference on Robotics and Automation (ICRA'2013).
A. Kapoor, M. Li, and R. H. Taylor, "Spatial Motion Constraints for Robot Assisted Suturing using Virtual Fixtures," 2005, vol. 3750, pp. 89-96.
A. Kapoor and R.H. Taylor, A Constrained Optimization Approach to Virtual Fixtures for Multi-Handed Tasks. In IEEE International Conference on Robotics and Automation (Pasadena, CA, 2008), pp. 3401-3406.
Agrawal, V., Peine, W. J., Yao, B., and Choi, S. Control of Cable Actuated Devices using Smooth Backlash Inverse. In 2010 IEEE International Conference on Robotics and Automation (Anchorage, AK, 2010), pp. 1074-1079.
Angeles, J. Automatic Computation of the Screw Parameters of Rigid-Body Motions. Part II: Infinitesimally-Separated Positions. Journal of Dynamic Systems, Measurement, and Control 108, Mar. 1986, 32-38.
Baki, P., Szekely, G., and Kosa, G. Miniature tri-axial force sensor for feedback in minimally invasive surgery. In 2012 4th IEEE RAS & EMBS In-ternational Conference on Biomedical Robotics and Biomechatronics (BioRob) (Roma, Italy, Jun. 2012), IEEE, pp. 805-810.
Bhattacharyya, S. (2011). Motion Planning and Constraint Exploration for Robotics Surgery. Master Thesis, Vanderbilt University, Nashville, TN.

Bhattacharyya, S. & Simaan, N (2013). Characterization of Constraints in Flexible Unknown Environments. In Accepted for publication in IEEE International Conference on Robotics and Automation (ICRA'2013).
Birkfellner, W., Watzinger, F., Wanschitz, F., Ewers, R., and Bergmann, H. Calibration of tracking systems in a surgical environment. IEEE Transactions on Medical Imaging 17, 5 (Oct. 1998), 737-42.
Bokelberg, E. H., Hunt, K. H., and Ridley, P. R. Spatial Motion-I: Points of inflection and the differential geometry of screws. Mechanism and Machine Theory 27, 1 (1992), 1-15.
Burgner, J., Swaney, P. J., Rucker, D. C., Gilbert, H. B., Nill, S. T., Russell III, P. T. R., Weaver, K. D., Iii, R. J. W., Russell, P. T., and Webster, R. J. A Bimanual Teleoperated System for Endonasal Skull Base Surgery. In 2011 IEEE International Conference on In-telligent Robots and Systems (San Francisco, CA, Sep. 2011), IEEE, pp. 2517-2523.
Camarillo, D. B., Carlson, C. R., and Salisbury, J. K. Configuration Tracking for Continuum Manipulators With Coupled Tendon Drive. IEEE Transactions on Robotics 25, 4 (Aug. 2009), 798-808.
Camarillo, D. B., Milne, C. F., Carlson, C. R., Zinn, M. R., and Salisbury, J. K. Mechanics Modeling of Tendon-Driven Continuum Manipulators. IEEE Transaction on Robotics 24, 6 (2008), 1262-1273.
Camarillo, D. B., Loewke, K., Carlson, C. R., and Salisbury, J. K. Vision based 3-D shape sensing of flexible manipulators. In 2008 IEEE International Conference on Robotics and Automation (Pasadena, CA, 2008), pp. 2940-2947.
Cauberg, E. C., de la Rosette, J. J., and de Reijke, T. M. How to improve the effectiveness of transurethral resection in nonmuscle invasive bladder cancer? Current Opinion in Urology 2 19, 5 (2009), 504-510.
Chan, T. F., and Dubey, R. V. A Weighted Least-Norm Solution Based Scheme for Avoiding Joint Limits for Redundant Joint Manipulators. IEEE Transaction on Robotics and Automation 11, 2 (1995), 286-292.
Chirikjian, G. S., and Burdick, J. W. A Modal Approach to Hyper-Redundant Manipulator Kinematics. IEEE Transaction on Robotics and Au-tomation 10, 3 (1994), 343-354.
Chirikjian, G. S., and Burdick, J. W. An obstacle avoidance algorithm for hyper-redundant manipulators. In Proceedings., IEEE International Conference on Robotics and Automation (1990), IEEE Comput. Soc. Press, pp. 625-631.
Croom, J. M., Rucker, D. C., Romano, J. M., and Webster, R. J. I. Visual Sensing of Continuum Robot Shape Using Self-Organizing Maps. In 2010 IEEE International Conference on Robotics and Automation (Anchorage, AK, 2010), pp. 4591-4596.
De Luca, A., Haddadin, S., and Hirzinger, G. Collision Detection and Safe Reaction with the DLR-III Lightweight Manipulator Arm. In 2006 IEEE/RSJ International Conference on Intelligent Robots and Systems (Beijing, China, 2006), pp. 1623-1630.
De Luca, A., and Manes, C. Modeling of Robots in Contact with a Dynamic Environment. IEEE Transaction on Robotics and Automation 10, 4 (1994), 542-548.
Degani, A., Choset, H., Wolf, A., and Zenati, M. A. Highly Articulated Robotic Probe for Minimally Invasive Surgery. In 2006 IEEE Inter-national Conference on Robotics and Automation (Orlando, FL, USA, 2006), pp. 4167-4172.
Dimaio, S. da Vinci and Beyond. In 2010 IEEE International Conference on Robotics and Automation Workshop on Medical Cyber-Physical Systems (Anchorage, AK, 2010).
Ding, J., Goldman, R. E., Xu, K., Allen, P. K, Fowler, D. L., and Simaan, N. Design and Coordination Kinematics of an Insertable Robotic Effectors Platform for Single-Port Access Surgery. IEEE/ASME Transactions on Mechatronics (2012), 1-13.
Dupont, P., Lock, J., Itkowitz, B., and Butler, E. Design and Control of Concentric-Tube Robots. IEEE Transaction on Robotics 26, 2 (2010), 209-225.
Eberman, B. S., and Salisbury, J. K. Determination of Manipulator Contact Information from Joint Torque Measurements. In Experimental Robotics I, vol. 139. Springer, 1990, pp. 463-473.
Featherstone, R. Modeling and Control of Contact Between Constrained Rigid Bodies. IEEE Transaction on Robotics and Automation 20, 1 (2004), 82-92.

(56) References Cited

OTHER PUBLICATIONS

Featherstone, R., Thiebaut, S. S., and Khatib, O. A General Contact Model for Dynamically-Decoupled Force/Motion Control. In 1999 IEEE International Conference on Robotics and Automation (1999), No. May, pp. 3281-3286.
Fine, H., Wei, W., Simaan, N., "Could Robots Ever Do Retina Surgery? ," Review of Ophthalmology, vol. 17, No. 5, Issue: May 1, 2010.
Fine, H., Wei, W., Chang, S. & Simaan, N (2009). A novel dual-arm dexterous ophthalmic microsurgical robot: applications for retinal vascular cannulation and stent deployment. In American Society of Retinal Specialists, Retina congress 2009, New York, NY, Sep. 4-Oct. 4.
Garty, G., Randers-Pehrson, G., Simaan, N., Salerno, A., A., D., J., N. et al (2007). Development of an ultrahigh-throughput robotically-based biodosimetry workstation using in-situ assays. In 13th International Congress of Radiation Research, San Francisco, California, Jul. 8-12, 2007.
Goldman, R. E. (2011). Analysis, Algorithms, and Control for Intelligent Surgical Exploration and Intervention. Phd Thesis, Columbia University (graduated with distinction).
Goldman, R. E., Bajo, A., Suh, L., Benson, M. & Simaan, N (2011). Rapidly Deployable Telerobotic Slave for Transurethral Exploration And Intervention. In presented in the 2011 Annual Engineering and Urology Society annual meeting, May 14, Washington, DC.
Goldman, R. E., Bajo, A. & Simaan, N. (2013). Algorithms for Autonomous Exploration and Estimation in Compliant Environments. Robotica, 31(1), 71-88.
Goldman, R. E., Bajo, A., MacLachlan, L. S., Pickens, R., Herrell, S. D. & Simaan, N. (2013). Design and Performance Evaluation of a Minimally Invasive Telerobotic Platform for Transurethral Surveillance and Intervention. IEEE Transactions on Biomedical Engineering, 60(4), 918-925.
Gravagne, I. A., and Walker, I. D. Kinematic Transformations for Remotely-Actuated Planar Continuum Robots. In 2000 IEEE International Conference on Robotics & Automation (San Francisco, 2000), No. Apr., pp. 19-26.
Guthart, G., and Salisbury, K. The IntuitiveTM Telesurgery System: Overview and Application. In 2000 IEEE International Conference on Robotics and Automation (2000), pp. 618-621.
Haddadin, S., De Luca, A., and Hirzinger, G. Collision Detection and Reaction: A Contribution to Safe Physical Human-Robot Interaction. In 2008 IEEE/RSJ International Conference on Intelligent Robots and Systems (Nice, France, 2008), pp. 3356-3363.
Herrell SD, Kwartowitz DM, Milhoua PM, Galloway RL. Toward Image-Guided Robotic Surgery: System Validation. J Urol. Feb. 2009; 181(2): 783-9 Discussion 789-90. Epub Dec. 16, 2008.
Ho, S. C., Hibberd, R. D., and Davies, B. L. Robot Assisted Knee Surgery. IEEE Engineering in Medicine and Biology Magazine 14, 3 (1995), 292-299.
Howell, L L. Compliant Mechanisms. Wiley-Interscience, 2001.
Ikits, M., Brederson, J. D., Hansen, C. D., and Hollerbach, J. M. An Improved Calibration Framework for Electromagnetic Tracking Devices. In 2001 IEEE Virtual Reality (Yokohama, Japan, 2001), IEEE Comput. Soc, pp. 63-70.
Ikuta, K., Yamamoto, K., and Sasaki, K. Development of remote micro-surgery robot and new surgical procedure for deep and narrow space. In 2003 IEEE International Conference on Robotics and Automation (Taipei, Taiwan, 2003), vol. 1, IEEE, pp. 1103-1108.
J. Zhang and N. Simaan, "Optimal Design of Under-actuated Steerable Electrode Arrays for Optimal Insertions," ASME Journal on Mechanisms and Robotics, Submitted , 2010.
J. Zhang, K. Xu, N. Simaan, and S. Manolidis, "A Pilot Study of Robot-Assisted Cochlear Implant Surgery Using Steerable Electrode Arrays," in International Conference on Medical Image Computing and Computer-Assisted Intervention (MICCAI '06), 2006, pp. 33-40.

J. Zhang, S. Manolidis, T. J. Roland, and N. Simaan, "Path Planning and Workspace Determination for Robot-Assisted Insertion of Steerable Electrode Arrays for Cochlear Implant Surgery," 2008.
J. Zhang, T. J. Roland, S. Manolidis, and N. Simaan, "Optimal Path Planning for Robotic Insertion of Steerable Electrode Arrays in Cochlear Implant Surgery," ASME Journal of Medical Devices, vol. 3, No. 1, 2009.
Zhang, J., Wei, W., Ding. J., Rolant, T.J., Manolidis, S., Simaan, N., "Inroads towards Robot-Assisted Cochlear Implant Surgery using Steerable Electrode Arrays", Otology & Neurology special issue on Cochlear Implants, doi: 10.1097/MAO.0b013e3181e7117e, 2010.
Zhang, J. (2010). Design of Steerable Electrode Arrays and Optimal Insertion Path Planning for Robot-Assisted Cochlear Implant Surgeries. Phd Thesis, Department of Mechanical Engineering, Columbia University, New York City, NY.
Jones, B. A., and Walker, I. D. Kinematics for Multisection Continuum Robots. IEEE Transactions on Robotics 22, 1 (Dec. 2006), 43-57.
K, Xu and N. Simaan, "Intrinsic Wrench Estimation and Its Performance Index for Multisegment Continuum Robots," IEEE Transactions on Robotics, vol. 26, No. 3, pp. 555-561, Jun. 2010.
Xu, K. (2009). Design, Modeling and Analysis of Continuum Robots as Surgical Assistants with Intrinsic Sensory Capabilities. Phd Thesis, Columbia University.
Xu, K, Qiu, D. & Simaan, N (2011). A Pilot Investigation of Continuum Robots as a Design Alternative for Upper Extremity Exoskeletons. In IEEE International Conference on Robotics and Biomimmetics (ROBIO'2011), pp. 656-662.
Kesner, S. B., and Howe, R. D. Design and Control of Motion Compensation Cardiac Catheters. In 2010 IEEE International Conference on Robotics and Automation (Anchorage, AK, 2010), pp. 1059-1065.
Kesner, S. B., and Howe, R. D. Force Control of Flexible Catheter Robots for Beating Heart Surgery. In 2011 IEEE International Conference on Robotics and Automation (Shanghai, China, Jan. 2011), pp. 1589-1594.
Kesner, S. B., Howe, R. D., and Member, S. Position Control of Motion Compensation Cardiac Catheters. IEEE Transaction on Robotics 27, 6 (2011), 1045-1055.
Khatib, O. A Unified Approach for Motion and Force Control of Robot Manipulators: The Operational Space Formulation. IEEE Journal of Robotics and Automation 3, 1 (1987), 43-53.
Kragic, D., Marayong, P., Li-Ming Su, Okamura, A. M., and Hager, G. D. Human-Machine Collaborative Systems for Microsurgical Applications. The International Journal of Robotics Research 24, 9 (Sep. 2005), 731-741.
Kwartowitz DM, Miga MI, Herrell SD, Galloway RL. Towards Image Guided Robotic Surgery: Multi-Arm Tracking Through Hybrid Localization. Int J Comput Assist Radiol Surg. May 2009;4(3):281-6. Epub Mar. 19, 2009.
L. B. Rosenberg, "Virtual fixtures: Perceptual tools for telerobotic manipulation," in Proceedings of IEEE Virtual Reality Annual International Symposium, 1993, pp. 76-82.
Lawson, G., Matar, N., Remade, M., Jamart, J., and Bachy, V. Transoral robotic surgery for the management of head and neck tumors: learning curve. European archives of oto-rhino-laryngology : official journal of the European Federation of Oto-Rhino-Laryngological Societies (EUFOS) : affiliated with the German Society for Oto-Rhino-Laryngology—Head and Neck Surgery 268, 12 (Dec. 2011), 1795-801.
Lipkin, H., and Duffy, J. Hybrid Twist and Wrench Control for a Robotic Manipulator. Transaction of the ASME 110 (1988), 138-144.
Lock, J., and Dupont, P. E. Friction Modeling in Concentric Tube Robots. In 2011 IEEE International Conference on Robotics and Automation (Shanghai, China, Jan. 2011), pp. 1139-1146.
Lumelsky, V. J., and Cheung, E. Real-Time Collision Avoidance in Tele-operated Whole-Sensitive Robot Arm Manipulators. IEEE Transactions on Systems, Man, and Cybernetics 23, 1 (1993), 194-203.
M. Li and R. H. Taylor, "Spatial Motion Constraints in Medical Robot Using Virtual Fixtures Generated by Anatomy," 2004, pp. 1270-1275.

(56) References Cited

OTHER PUBLICATIONS

Ma, S., and Konno, M. An obstacle avoidance scheme for hyper-redundant manipulators-global motion planning in posture space. In Proceedings of Inter-national Conference on Robotics and Automation (1997), vol. 1, IEEE, pp. 161-166.

Mahvash, M., and Okamura, A. M. Friction Compensation for a Force-Feedback Telerobotic System. In 2006 IEEE International Conference on Robotics and Automation (Orlando, FL, 2006), No. May, pp. 3268-3273.

Mahvash, M., and Dupont, P. E. Mechanics of dynamic needle insertion into a biological material. IEEE transactions on biomedical engineering 57, 4 (Apr. 2010), 934-43.

Mahvash, M., and Dupont, P. E. Stiffness Control of Surgical Continuum Manipulators. IEEE Transaction on Robotics 27, 2 (2011), 334-345.

Mason, M. T. Compliance and Force Control for Computer Controlled Manipulators. IEEE Transaction on Systems, Man, and Cybernetics smc-11, 6 (1981), 418-432.

Mason, M. T., and Salisbury, J. K. Robot Hands and the Mechanics of Manipulation. MIT Press, Cambridge, MA, 1985.

Matsumoto, T., and Kosuge, K. Collision Detection of Manipulator Based on Adaptive Control Law. In 2001 IEEE/ASME International Conference on Advanced Intelligent Mechatronics (Como, Italy, 2001), pp. 177-182.

N. Simaan, R. Taylor, and P. Flint, "A Dexterous System for Laryngeal Surgery—Multi-Backbone Bending Snake-like Slaves for Teleoperated Dexterous Surgical Tool Manipulation." pp. 351-357, 2004.

N. Simaan, R. Taylor, P. Flint, and A. Hillel, "Minimally Invasive Surgery of the Upper Airways: Addressing the Challenges of Dexterity Enhancement in Confined Spaces," Nova Scien, R. Faust, Ed. 2007, pp. 261-280.

N. Simaan, W. Wei, R. Goldman, H. Fine, and S. Chang, "A Dual-Arm Workstation for Intraocular Dexterity-Enhanced Microsurgery of the Eye and In-Organ Dexterity Enhancement and Manipulation of Suspended Organs," 2006.

N. Simaan and M. Shoham, "Geometric Interpretation of the Derivatives of Parallel Robot's Jacobian Matrix with Application to Stiffness Control" ASME Journal of Mechanical Design, vol. 125, pp. 33-42., doi: 10.1115/1.1539514, 2003.

N. Simaan and M. Shoham, "Singularity Analysis of a Class of Composite Serial In-Parallel Robots," IEEE transactions on Robotics and Automation, vol. 17, No. 3, pp. 301-311, doi:10.1109/70.938387 Jun. 2001.

N. Simaan and M. Shoham, "Stiffness Synthesis of a Variable Geometry Six Degrees-of-Freedom Double Planar Parallel Robot," International Journal of Robotics Research (IJRR), vol. 22, No. 9, pp. 757-775, doi: 10.1177/02783649030229005, Sep. 2003.

N. Simaan, K. Xu, W. Wei, A. Kapoor, P. Kazanzides, R. Taylor, P. Flint, "Design and Integration of a Telerobotic System for Minimally Invasive Surgery of the Throat," International Journal of Robotics Research (IJRR) special issue on medical robotics. doi: 10.1177/0278364908104278, vol. 28, No. 9, 1134-1153 , 2009.

Simaan, N., Manolidis, S. & Roland, J. T (2009). Inroads towards a robotically inserted CI electrode development. In 9th European Symposium of Paediatric Cochlear Implantation.

Simaan, N., Zhang, J., Roland, J. T. & Manolidis, S (2010). Steerable Continuum Robot Design for Cochlear Implant Surgery. In IEEE International Conference on Robotics and Automation Workshop on Snakes, Worms, and Catheters: Continuum and Serpentine Robots for Minimally Invasive Surgery, May 3.

Simaan, N., Zhang, J., Roland, J. T. & Manolidis, S (2010). Robotic Study Shows that Insertion Speed Affects Cochlear Implant Electrode Insertion Forces. In the 11th International Conference on Cochlear Implants and other Implantable Auditory Technologies, Stockholm, Sweden, Jun. 30-Jul. 3.

Simaan, N., Zhang, J., Roland, J. T. & Manolidis, S (2011). Robotic System for Steerable Cochlear Implant Insertion. In 2011 National Congress of the Italian Society of Audiology & Phoniatrics in Bari, Italy.

Simaan, N (2012). Design Considerations and Lessons Learned in Developing Systems for Single Port Access Surgery and Natural Orifice Surgery. In 34th international Conference on Engineering in Medicine and Biology Society (mini-symposium on Robotic Single-Port Surgery and NOTES). San Diego, Aug. 27-31, 2012.

Simaan, N., Bajo, A., Reiter, A., Long, W., Allen, P. & Fowler, D. (2013). Lessons learned using the insertable robotic affector platform (IREP) for single port access surgery. Journal of Robotic Surgery.

Nakamura, Y. Advanced Robotics: Redundancy and Optimization. Addison-Wesley Longman Publishing Co., Inc., Boston, MA, USA, 1990.

Park, J., and Khatib, O. Robot Multiple Contact Control. Robotica 26, 05 (2008), 667-677.

Penning, R. S., Jung, J., Borgstadt, J. A., Ferrier, N. J., and Michael, R. Towards Closed Loop Control of a Continuum Robotic Manipulator for Medical Applications. In 2011 IEEE International Conference on Robotics and Automation (Shanghai, China, 2011), pp. 4822-4827.

Petrovskaya, A., Park, J., and Khatib, O. Probabilistic Estimation of Whole Body Contacts for Multi-Contact Robot Control. In 2007 IEEE International Conference on Robotics and Automation (Rome, 2007), No. c, pp. 568-573.

Phee, S. J., Low, S. C., Sun, Z. L, Ho, K. Y., Huang, W. M., and Thant, Z. M. Robotic system for no-scar gastrointestinal surgery. The international journal of medical robotics + computer assisted surgery : MRCAS 4, 1 (Mar. 2008), 15-22.

Piccigallo, M., Scarfogliero, U., Quaglia, C., Petroni, G., Val-dastri, P., Menciassi, A., and Dario, P. Design of a Novel Bimanual Robotic System for Single-Port Laparoscopy. IEEE/ASME Transaction on Mechatronics 15, 6 (2010), 871-878.

Pile, J., Tsay, I. A., Dalton, J., Balachandran, R., Labadie, R. F. & Simaan, N (2012). Speed Dependence of Insertion Forces During CI Electrode Insertion, In Presented at the 12th Annual Conference on Cochlear Implants and other Implantable Auditory Technologies CI'2012, Baltimore, MD, May 3-5, 2012.

Pile, J. & Simaan, N (2013). Characterization of Friction and Speed Effects and Methods for Detection of Cochlear Implant Electrode Tip Fold-over. In Accepted for publication in IEEE International Conference on Robotics and Automation (ICRA'2013).

R.H. Sturges Jr and S. Laowattana, "A flexible, tendon-controlled device for endoscopy," 1991, vol. 3, pp. 2582-2591.

Raibert, M. H., and Craig, J. J. Hybrid Position/Force Control of Manipulators. Journal of Dynamic Systems, Measurement, and Control 103, 2 (1981), 126.

Reichert, S., Zhang, J., Xu, K, Simaan, N. & Manolidis, S (2007). Robotic insertion of cochlear implant electrodes to minimize cochlear trauma. In 6th European Congress of Oto-Rhino-Laryngology, Head and Neck Surgery., Vienna, Austria, Jun. 2007.

Robinson, G., and Davies, J. Continuum robots—a state of the art. In 1999 IEEE International Conference on Robotics and Automation (Detroit, MI, USA, 1999), vol. 4, Ieee, pp. 2849-2854.

Roland, J. T., Zhang, J., Manolidis, S. & Simaan, N (2009). Progress Towards A Robotically Inserted Cochlear Implant Electrode. In 12th Symposium on Cochlear Implants in Children, Seattle.

Rosenberg, L. Virtual fixtures: Perceptual tools for telerobotic manipulation. In Proceedings of IEEE Virtual Reality Annual International Symposium (1993) pp. 76-82.

Rucker, D. C., and Webster, III, R. J. Deflection-Based Force Sensing for Continuum Robots : A Probabilistic Approach. In 2011 IEEE/RSJ Inter-national Conference on Intelligent Robots and Systems (2011), pp. 3764-3769.

Rucker, D. C., Jones, B. A., and Webster III, R. J. A Geometrically Exact Model for Externally Loaded Concentric-Tube Continuum Robots. IEEE Transaction on Robotics 26, 5 (2010), 769-780.

S. J. Harris, W. J. Lin, R. D. Hibberd, J. Cobb, R. Middelton, and B. L. Davies, "Experiences with Robotic Systems for Knee Surgery," vol. 1205, J. Troccaz, E. Grimson, and R. Mosges, Eds. Springer, 1997, pp. 757-766.

Saito, S. Transurethral en bloc resection of bladder tumors. The Journal of urology 166, 6 (Dec. 2001), 2148-50.

Salerno, A., Zhang, J., Bhatla, A., Lyulko, O. V., Nie, J., Dutta, A. et al (2007). Design Considerations for a Minimally Invasive

(56) References Cited

OTHER PUBLICATIONS

High-Throughput Automation System for Radiation Biodosimetry. In IEEE Conference on Automation Science and Engineering, pp. 846-852. Scottsdale, AZ, USA.

Salisbury, J. Active stiffness control of a manipulator in cartesian coordinates. In 1980 19th IEEE Conference on Decision and Control including the Symposium on Adaptive Processes (1980), pp. 95-100.

Seibold, U., Kubler, B., and Hirzinger, G. Prototype of Instrument for Minimally Invasive Surgery with 6-Axis Force Sensing Capability. In Proceedings of the 2005 IEEE International Conference on Robotics and Automation (Barcelona, Spain, 2005), 496-501, Ed., IEEE, pp. 496-501.

Sentis, L., Park, J., and Khatib, O. Compliant Control of Multicontact and Center-of-Mass Behaviors in Humanoid Robots. IEEE Transactions on Robotics 26, 3 (Jun. 2010), 483-501.

Shen, J.-H., Yu, H., Simaan, N. & Joos, K. M. (2013). A Robotic-controlled Intraocular OCT Probe. In 2013 The Association for Research in Vision and Ophthalmology Annual Conference (ARVO'2013).

Siciliano, B., Sciavicco, L., Villani, L., and Oriolo, G. Robotics: Modelling, Planning, and Control. 2009.

Su, H., Cardona, D. C., Shang, W., Camilo, A., Cole, G. A., Rucker, D. C., Webster, R. J., and Fischer, G. S. A MRI-Guided Concentric Tube Continuum Robot with Piezoelectric Actuation: A Feasibility Study. In 2012 IEEE International Conference on Robotics and Automation (St. Paul, MN USA, 2012), No. May.

Taylor, R., Jensen, R, Whitcomb, L., Barnes, A., Kumar, R., Stoianovici, D., Gupta, P., Wang, Z., DeJuan, E., and Kavoussi, L. A Steady-hand robotic system for microsurgical augmentation. International Journal of Robotics Research 18, 12 (1999), 1201-1210.

Torres, L G., and Alterovitz, R. Motion Planning for Concentric Tube Robots Using Mechanics-based Models. In 2011 IEEE/RSJ International Con-ference on Intelligent Robots and Systems (San Francisco, CA, USA, 2011), pp. 5153-5159.

Ukai, R., Kawashita, E., and Ikeda, H. A new technique for transurethral resection of superficial bladder tumor in 1 piece. The Journal of Urology2 163, 3 (2000), 878-879.

Valdastri, P., Harada, K., Menciassi, A., Beccai, L., Stefanini, C., Fujie, M., and Dario, P. Integration of a miniaturised triaxial force sensor in a minimally invasive surgical tool. IEEE transactions on biomedical engineering 53, 11 (Nov. 2006), 2397-400.

W. Wei, R. Goldman, H. Fine, S. Chang, and N. Simaan, "Design and Dexterity Evaluation for a Dual-Arm Micro-Surgical Robotic System for Orbital Manipulation and Intraocular Dexterity," IEEE Transactions on Robotics, vol. 25, No. 1, pp. 147-157, 2009.

Wagner, C. R., Stylopoulos, N., Jackson, P. G., and Howe, R. D. The Benefits of Force Feedback in Surgery: Examination of Blunt Dissection. Presence: Teleoperators and Virtual Environments 16, 3 (2007), 252-262.

Webster III, R. J., Romano, J. M., and Cowan, N. J. Mechanics of Precurved-Tube Continuum Robots. IEEE Transaction on Robotics 25, 1 (2009), 67-78.

Webster III, R. J., and Jones, B. A. Design and Kinematic Modeling of Constant Curvature Continuum Robots: A Review. The International Journal of Robotics Research (Jun. 2010).

Wei Tech, A., Khosla, P., and Riviere, C. An Intelligent Hand-Held Microsurgical Instrument for Improved Accuracy. In 23rd Annual International Conference of the IEEE Engineering in Medicine and Biology Society (Istanbul, Turkey, 2001), pp. 25-28.

Wei, W., Goldman, R., Fine, H., Chang, S., Simaan, N., "Performance Evaluation for Multi-Arm Manipulation of Hollow Suspended Organs," IEEE Transactions on Robotics, vol. 25, No. 1, pp. 147-157, doi 10.1109/TRO.2008.2006865, 2009.

Wei, W., Simaan N., "Design of Planar Parallel Robots With Preloaded Flexures for Guaranteed Backlash Prevention," ASME Journal of Mechanisms and Robotics (JMR), doi:10.1115/1.4000522, vol. 2, No. 1, pp. 011012-1 to 011012-10, 2010.

Wei, W. (2010). Design and Implementation of High-Precision Hybrid Robotic Systems with Application for Ophthalmic Micro-Surgery. Phd Thesis, Department of Mechanical Engineering, Columbia University, New York City, NY.

Wei, W., Fine, H., Chang, S. & Simaan, N (2010). A Pilot Study on Using a Flexible Cannula Robot for Micro-Vascular Stenting. In IEEE International Conference on Robotics and Automation Workshop on Snakes, Worms and Catheters: Continuum and Serpentine Robots for Minimally Invasive Surgery, IEEE International Conference on Robotics and Automation, May 3.

Weinstein, G. S., O'Malley, B. W., Magnuson, J. S., Carroll, W. R., Olsen, K. D., Daio, L., Moore, E. J., and Holsinger, F. C. Transoral robotic surgery: A multicenter study to assess feasibility, safety, and surgical margins. The Laryngoscope (Jul. 2012), 1-7.

Whitney, D. E. Force Feedback Control of Manipulator Fine Motions. Journal of Dynamic Systems, Measurement, and Control 99, 2 (1977), 91.

Whitney, D. E. Resolved Motion Rate Control of Manipulators and Human Prostheses. IEEE Transaction on Man-Machine Systems MMS-10, 2 (Jun. 1969), 47-53.

Yoshikawa, T. Force Control of Robot Manipulators. In 2000 IEEE International Conference on Robotics and Automation (San Francisco, CA, USA, 2000), No. Apr., pp. 220-226.

Yu, H., Shen, J. H., Joos, K. M. & Simaan, N (2013). Design , Calibration and Preliminary Testing of A Robotic Telemanipulator for OCT guided Retinal Surgery. In Accepted for publication in IEEE International Conference on Robotics and Automation (ICRA'2013).

Zhou, J., Shen, X., Petriu, E. M., and Georganas, N. D. Linear Velocity and Acceleration Estimation of 3 DOF Haptic Interface. In IEEE International Workshop on Haptic Audio Visual Environments and their Application (HAVE 2008) (Ottawa, Canada, 2008), pp. 137-142.

International Search Report and Written Opinion for PCT Application No. PCT/US2013/021167 dated Mar. 22, 2013.

International Search Report and Written Opinion for PCT Application No. PCT/US2013/037346 dated Aug. 27, 2013.

International Search Report and Written Opinion for PCT Application No. PCT/US2013/037353 dated Aug. 19, 2013.

International Search Report and Written Opinion for PCT Application No. PCT/US2013/039280 dated Aug. 20, 2013.

U.S. Office action for U.S. Appl. No. 13/891,389 dated Jan. 2, 2015.

A. Bajo and N. Simaan, "Finding Lost Wrenches: Using Continuum Robots for Contact Detection and Estimation of Contact Location," 2010 IEEE International Conference on Robotics and Automation (May 3-8, 2010).

Bajo, A., Goldman, R. E., Wang, L, Fowler, D. & Simaan, N (2012). Integration and Preliminary Evaluation of an Insertable Robotic Effectors Platform for Single Port Access Surgery. In International Conference on Robotics and Automation (ICRA'2012), pp. 3381-3387.

Bajo, A., Pickens, R. B., Herrell, D. S. & Slmaan, N (2012). A Pilot Ex-Vivo Evaluation of a Telerobotic System for Transurethral Intervention and Surveillance. In Hamlyn Symposium on Medical Robotics.

Bajo, A., Pickens, R. B., Herrell, D. S. & Simaan, N (2013). Constrained Motion Control of Multisegment Continuum Robots for Transurethral Bladder Resection and Surveillance. In Accepted for publication in IEEE International Conference on Robotics and Automation (ICRA'2013).

A. Kapoor, K. Xu, W. Wei, N. Simaan, and R. Taylor, "Telemanipulation of Snake-Like Robots for Minimally Invasive Surgery of the Upper Airway," in MICCAI 2006 workshop on medical robotics, 2006.

A. Kapoor, N. Simaan, and P. Kazanzides, "A System for Speed and Torque Control of DC Motors with Application to Small Snake Robots," 2004.

A. Kapoor, N. Simaan, and R. Taylor, "Suturing in Confined Spaces: Constrained Motion Control of a Hybrid 8-DoF Robot", in IEEE Conference on Advanced Robotics, 2005, pp. 452-459.

Abbott, J., Marayong, P., and Okamura, A. M. Haptic virtual fixtures for robot-assisted manipulation. Robotics Research 28, Aug. 2007, 49-64.

(56) References Cited

OTHER PUBLICATIONS

Alexander T. Hillel, Ankur Kapoor, Nabil Simaan, Russell H. Taylor and Paul Flint, "Applications of Robotics for Laryngeal Surgery," Otolaryngologic Clinics of North America, Nasir Bhatti & Ralph P. Tufano Eds., vol. 41, Issue 4, pp. 781-791, doi:0.1016/j.otc.2008.01.021, Aug. 2008.

Chen, Y., Zhang, J., Wang, H., Garty, G., Xu, Y., Lyulko, O., Turner, H., Randers-Pehrson, G., Simaan, N., Yao, L., Brenner, D., "Development of a Robotically-based Automated Biodosimetry Tool for Highthroughput Radiological Triage," accepted in International Journal of Biomechatronics and Biomedical Robotics (IJBBR), vol. 1, No. 2 pp. 115-125, 2010.

Debus, T., Dupont, P., and Howe, R. Contact State Estimation using Multiple Model Estimation and Hidden Markov Models. 2The International Journal of Robotics Research 23, 4-5 (2004), 399-413.

Ding, J., Xu, K., Goldman, R. E., Allen, P. K., Fowler, D. L., and Simaan, N. "Design, Simulation and Evaluation of Kinematic Alternatives for Insertable Robotic Effectors Platforms in Single Port Access Surgery," In 2010 IEEE International Conference on Robotics and Automation (Anchorage, AK, 2010), pp. 1053-1058.

Godage, Isuru S. et al., "Shape Function-Based Kinematics and Dynamics for Variable Length Continuum Robotic Arms," 2011 IEEE International Conference on Robotics and Automation (May 9-13, 2011).

R. E. Goldman, A. Bajo, and N. Simaan, "Compliant Motion Control for Continuum Robots with Intrinsic Actuation Sensing," in IEEE International Conference on Robotics and Automation, 2011, pp. 1126-1132.

Gravagne, Ian A. and Ian D. Walker, "Manipulability, Force, and Compliance Analysis for Planar Continuum Manipulators," IEEE Transactions on Robotics and Automation, vol. 18, No. 3 (Jun. 2002).

Gravagne, Ian A. et al, "Good Vibrations: A Vibration Damping Setpoint Controller for Continuum Robots," Proceedings of the 2001 IEEE International Conference on Robotics & Automation (May 21-26, 2001).

Hamid, S. A. & Simaan, N (2009). Design and Synthesis of Wire-Actuated Universal-Joint Wrists for Surgical Applications. In 2009 IEEE International Conference on Robotics and Automation, pp. 1807-1831. Kobe, Japan.

Hannan, M. W., and Walker, I. D. Kinematics and the Implementation of an Elephant's Trunk Manipulator and Other Continuum Style Robots. Journal of Robotic Systems 20, 2 (2003), 45-63.

Hayward, Vincent, "Fast Collision Detection Scheme by Recursive Decomposition of A Manipulator Workspace," Proceedings IEEE International Conference on Robotics and Automation, vol. 3 (1986).

Hogan, N. Impedance Control: An Approach to Manipulation: Part ITheory. Journal of Dynamic Systems, Measurement, and Control 107, 1 (1985), 1.

J. Ding, K. Xu, R. Goldman, P. Allen, D. Fowler, and N. Simaan, "Design, Simulation and Evaluation of Kinematic Alternatives for Insertable Robotic Effectors Platforms in Single Port Access Surgery." pp. 1053-1058, 2010.

J. J. Abbott and A. M. Okamura, "Stable Forbidden-Region Virtual Fixtures for Bilateral Telemanipulation," vol. 128, No. 1, pp. 53-64, 2006.

J. Zhang, S. Bhattacharyya, and N. Simaan, "Model and Parameter Identification of Friction During Robotic Insertion of Cochlear-Implant Electrode Arrays," in IEEE International Conference on Robotics and Automation, 2009, pp. 3859-3864.

Jones, Bryan A., "Kinematics for Multisection Continuum Robots," IEEE Transactions on Robotics, vol. 22, No. 1 (Feb. 2006).

K. Xu and N. Simaan, "Actuation Compensation for Flexible Surgical Snake-like Robots with Redundant Remote Actuation," in IEEE International Conference on Robotics and Automation, 2006, pp. 4148-4154.

K. Xu and N. Simaan, "Analytic Formulation for Kinematics, Statics and Shape Restoration of Multibackbone Continuum Robots via Elliptic Integrals," ASME Journal of Mechanisms and Robotics (JMR), vol. 2, pp. 11006-11013, 2010.

K. Xu, R. Goldman, J. Ding, P. Allen, D. Fowler, and N. Simaan, "System Design of an Insertable Robotic Effector Platform for Single Port Access (SPA) Surgery," in IEEE/RSJ International Conference on Intelligent Robots and Systems, 2009, pp. 5546-5552.

K. Xu and N. Simaan, "An Investigation of the Intrinsic Force Sensing Capabilities of Continuum Robots," IEEE Transactions on Robotics (TRO), vol. 23, No. 3 (Jun. 2008).

Mahvash, Mohsen and Pierre E. Dupont, "Stiffness Control of a Continuum Manipulator in Contact with a Soft Environment," The 2010 IEEE/RSJ International Conference on Intelligent Robots and Systems (Oct. 18-22, 2010).

Mahvash, Mohsen and Pierre E. Dupont, "Stiffness Control of Surgical Continuum Manipulators," IEEE Transactions on Robotics, vol. 27, No. 2 (Apr. 2011).

N. Simaan, A. Bajo, A. Reiter, L. Wang, P. Allen, and D. Fowler, "Lessons learned using the insertable robotic effector platform (IREP) for single port access surgery," Journal of Robotic Surgery, Apr. 2013.

N. Simaan, "Snake-Like Units Using Flexible Backbones and Actuation Redundancy for Enhanced Miniaturization," In 2005 IEEE International Conference on Robotics and Automation (Barcelona, Spain, 2005), IEEE, pp. 3023-3028.

N. Simaan, Russell H. Taylor, Paul Flint, "High Dexterity Snake-like Robotic Slaves for Minimally Invasive Telesurgery of the Upper Airway," MICCAI 2004 (7th International Conference on Medical Image Computing and Computer-Assisted Intervention), pp. 17-24, vol. 2, Saint Malo, France, Sep. 26-30, 2004.

Simaan, N., Glozman, D. & Shoham, M (1998). Design Considerations of New Six Degrees-Of-Freedom Parallel Robots. In IEEE International Conference on Robotics and Automation (ICRA'1998), pp. 1327-1333.

Simaan, N. (1999). Analysis and Synthesis of Parallel Robots for Medical Applications. Master Thesis, Technion-Israel Institute of Technology, Haifa, Israel.

N. Simaan, Task-Based Design and Synthesis of Variable Geometry Parallel Robots (2002). Phd Thesis, Technion-Israel Institute of Technology, Haifa, Israel.

Pickens, R. B., Bajo, A., Simaan, N. & Herrell, S. D (2012). Preliminary Testing of a Transurethral Dexterous Robotic System for Bladder Resection. In 27th EUS Annual Meeting, pp. 65. Atlanta, GA.

Pile, J., Cheung, M.-Y., Zhang, J. & Simaan, N (2011). Algorithms and Design Considerations for Robot Assisted Insertion of Perimodiolar Electrode Arrays. In 2011 IEEE International Conference on Robotics and Automation. Shanghai, China.

R. Taylor et al., "Steady-hand robotic system for microsurgical augmentation," International Journal of Robotics Research, vol. 18, No. 12, pp. 1201-1210, 1999.

Reiter, A., Bajo, A., Iliopoulos, K., Simaan, N., and Allen, P. K. Learning-Based Configuration Estimation of a Multi-Segment Continuum Robot. In The Fourth IEEE RAS/EMBS International Conference on Biomedical Robotics and Biomechatronics (Roma, Italy, 2012), p. accepted.

Reiter, A., Goldman, R. E., Bajo, A., Iliopoulos, K., Simaan, N., and Allen, P. K. A Learning Algorithm for Visual Pose Estimation of Continuum Robots. In 2011 IEEE/RSJ International Conference on Intelligent Robots and Systems (San Francisco, CA, USA, 2011), pp. 2390-2396.

Rivera-Serrano, C. M., Johnson, P., Zubiate, B., Kuenzler, R., Choset, H., Zenati, M., Tully, S., and Duvvuri, U. A transoral highly flexible robot: Novel technology and application. The Laryngoscope 122, 5 (May 2012), 1067-71.

Sen, T. H., Deshmukh, N., Roger E, .. G., Kazanzides, P., Taylor, R. H., Boctor, E. et al (2012). Enabling technologies for natural orifice transluminal endoscopic surgery (N.O.T.E.S) using robotically guided elasticity imaging. In Proceeding of SPIE Medical Imaging 2012, pp. 83161Y1-83161Y8.

Tully, S., Bajo, A., Kantor, G., Choset, H., and Simaan, N. Constrained Filtering with Contact Detection Data for the Localization

(56) References Cited

OTHER PUBLICATIONS and Registration of Continuum Robots in Flexible Environments. In 2012 IEEE International Conference on Robotics and Automation (St. Paul, MI USA, 2012).

W. Wei, K. Xu, and N. Simaan, "A compact Two-armed Slave Manipulator for Minimally Invasive Surgery of the Throat," in IEEE RAS/EMBS International Conference on Biomedical Robotics and Biomechatronics, 2006, pp. 769-774.

Wei, W., Goldman, R. E., Simaan, N., Fine, H. & Chang, S (2007). Design and Theoretical Evaluation of Micro-Surgical Manipulators for Orbital Manipulation and Intraocular Dexterity. In 2007 IEEE International Conference on Robotics and Automation, pp. 3389-3395. Roma, Italy.

Wei, W., and Simaan, N. Modeling, Force Sensing, and Control of Flexible Cannulas for Microstent Delivery. Journal of Dynamic Systems, Measurement, and Control 134, 4 (2012), 041004.

Wei, W., Popplewell, C., Fine, H., Chang, S., Simaan, N., "Enabling Technology for Micro-Vascular Stenting in Ophthalmic Surgery," ASME Journal of Medical Devices (JMED), vol. 4, Issue 1, 014503 (6 pages) doi:10.1115/1.4001193, 2010.

U.S. Office action for U.S. Appl. No. 14/271,418 dated May 20, 2015.

International Search Report, PCT/US2013/037336, dated Jul. 25, 2013.

Written Opinion, PCT/US2013/037336, dated Jul. 25, 2013.

\* cited by examiner

DEXTEROUS WRISTS FOR SURGICAL INTERVENTION

RELATED APPLICATIONS

This application claims priority to U.S. Provisional Application No. 61/636,001, filed on Apr. 20, 2012 and titled "DEXTEROUS WRISTS FOR SURGICAL INTERVENTION," the entire contents of which are incorporated herein by reference.

STATEMENT REGARDING FEDERALLY SPONSORED RESEARCH OR DEVELOPMENT

This invention was made with government support under grant 7R21EB007779-04 awarded by National Institutes of Health. The government has certain rights in the invention.

FIELD OF THE INVENTION

The present invention relates to dexterous gripping devices and surgical wrists. In particular, the invention relates to gripper assemblies with integrated axial rotation capabilities, selective detachability, and roll-yaw-pitch wrist action for use with robotic systems during minimally invasive surgical procedures.

SUMMARY

In one embodiment, the invention provides a continuum robot including a plurality of controllably bending continuum robot segments, a gripper, and a wrist. The continuum robot has tubular shafts (backbones) that actuate its segments to cause it to bend and also provide an actuation pathway for the gripper and the wrist. The gripper is selectively connectable to the distal end of the continuum robot (hereafter referred to as the end disk). A rotatable wrist connects the gripper to the end disk. The rotatable wrist includes a hub that is selectively connectable to the end disk. A wrist capstan is rotatably connected to the wrist hub and non-rotatably connected to the gripper base. A flexible wire rope enters the wrist hub through one tubular shaft (backbone), wraps around the wrist capstan and then returns though a second tubular shaft (backbone) of the continuum robot. This wire rope makes a closed loop distally connected to the wrist capstan and proximally connected to an actuation unit with a linear actuator and a tensioning idler pulley. Linear movement of the actuator causes linear movement of the flexible wire loop through the shafts of the continuum robot and thus causes rotation of the wrist capstan due to friction between the flexible wire loop and the wrist capstan.

In some embodiments, the wrist capstan includes a grooved surface and the flexible wire loop includes a spherical feature that meshes inside a matching grooved surface in the wrist capstan. In some such embodiments, the wire does not make a full turn around the capstan and torque transmission to the capstan relies on the positive lock between the spherical feature and the capstan rather than on friction between the wire rope and the capstan.

In some embodiments the wire rope is routed on idler pulleys in the wrist hub. The wire rope enters the wrist hub through one continuum robot shaft, bends on the circumference of a first idler pulley tangentially oriented to the wrist capstan, wraps fully or partially around the capstan, and returns on a second idler pulley in a similar manner into a second continuum robot shaft (backbone).

In some embodiments the idler pulleys are replaced by curved surfaces in the wrist hub in order to reduce size and cost. The wire rope then slides on these curved surfaces and wraps around the capstan. The curved surfaces may be treated with friction reducing treatments such as PTFE coatings or hard anodize treatment. The curved surface geometry is uniquely determined such that the first curved surface where the wire rope enters the wrist hub is placed at a height difference compared to the second curved surface where the wire rope exits the wrist hub. This axial height difference is determined by the pitch of the helical path of the wire rope winding around the capstan.

In some embodiments, the wrist hub includes a first helical circumferential groove and a second helical circumferential groove in the wrist hub. These grooves replace the function of the idler pulleys and allow transmission of the wire rope from the entry point of the wrist hub along the first helical path to a point of tangency to the wrist capstan and then returning to the second helical groove to the exit shaft in the continuum robot In some embodiments the wrist capstan is made of two parts comprising of a capstan shaft and a capstan ring. The capstan ring is attached to the capstan shaft in a manner that allows transmission of torque but does not allow transmission of axial motion. Such embodiment may include a spline shaft. In this design the capstan is allowed to move axially to conform with the movement of the helically wound wire rope loop.

In some embodiments the wrist base (hub) is attached to the end disk of the continuum robot through a revolute articulated joint (herein called pitch axis). Actuation of the wrist is achieved through a wire rope loop that passes through two backbones (shafts) of the continuum robot while bending of the pitch axis is achieved via a push-pull superelastic NiTi wire that passes through a third shaft of the continuum robot or via a wire rope loop that passes through two opposing shafts of the continuum robot.

In some embodiments the wrist base (hub) is attached to the end disk of the continuum robot through a universal (Cardan) articulated joint that provides bending in the yaw and pitch axes. Actuation of the wrist (roll axis) is achieved through a wire rope loop that passes through two backbones (shafts) of the continuum robot while bending of the pitch axis is achieved via a push-pull superelastic NiTi wire that passes through a third shaft of the continuum robot. Similarly, bending of the yaw axis is achieved via a push-pull superelastic NiTi wire that passes through a third shaft of the continuum robot.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Some surgical tools, such as described in U.S. Pub. No. 2011/0230894, which is incorporated herein by reference, include continuum robots with gripping tools connected to the distal end of the continuum robot. A continuum robot is a snake-like robot with a plurality of segments. The segments are controlled independently to adjust the shape and position of the continuum robot. Although some of these tools include articulated wrists for adjusting the position of the gripper, the existing tools are incapable of producing instrument roll about the gripper axis. This limits implementation of these devices for highly precise manipulations such as micro-surgery since very exact coordinated motion of several degrees of freedom is required.

Figure 1:
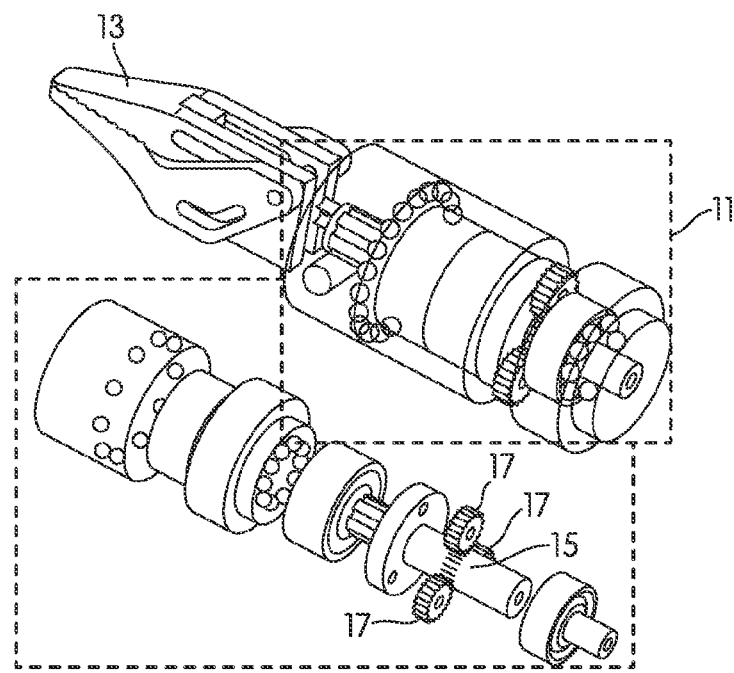
FIG. 1 is an exploded view of a rotatable gripper wrist according to one embodiment.

FIG. 1 illustrates a first example of an articulated wrist 11 that is capable of rotating the gripper 13 relative to the shaft (or plurality of segments) of a continuum robot or other device. The example of FIG. 1 is achieved using microplanetary gears. The sun gear 15 is actuated through a miniature torsional shaft and the planetary gears 17 amplify this torque and rotate the wrist about its axis.

Figure 2:
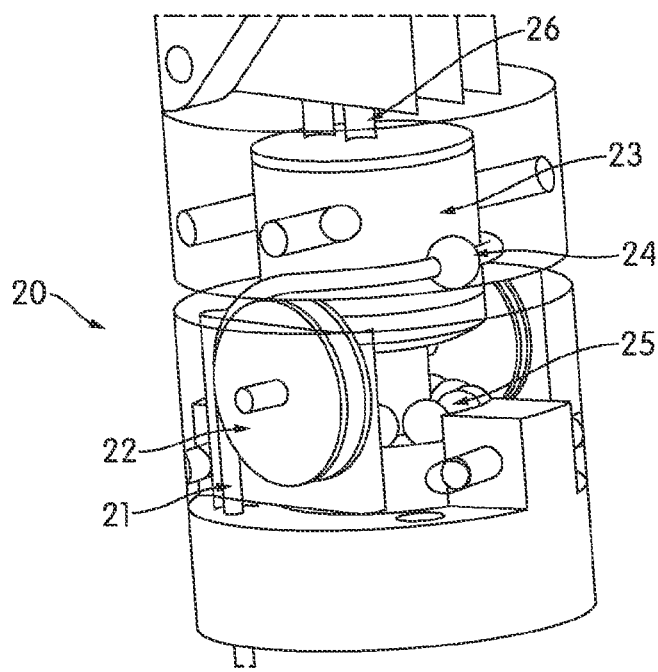
FIG. 2 is a view of a rotatable gripper wrist according to another embodiment.

FIG. 2 shows a different construction of a wrist assembly 20 that uses a miniature pulley with wire actuation to achieve rotation of the gripper. As illustrated, the ends of a wire loop 21 each pass across a pulley 22 extending into the shaft of the continuum robot. The wire loop is then positioned around a textured or grooved capstan assembly 23. As either end of the flexible wire loop 21 is inserted and retracted from the shaft of the continuum robot, the friction between the wire loop 21 and the capstan assembly 23 causes the capstan assembly to rotate relative to the shaft of the continuum robot. This rotation also causes the gripper to rotate. The ends of the wire loop extend through tubular structures in the shaft of the continuum robot called secondary backbones. The wire loop in the example of FIG. 2 includes a positive-locking, spherical shaped terminal 24 that is crimped on the flexible wire. The terminal 24 causes increased frictions between the flexible wire 21 and the capstan 23. The flexible wire in this example is a NiTi wire.

A plurality of ball bearings 25 are incorporated into the wrist assembly 200 to provide for smooth rotation of the capstan assembly 23 and, as a result, the gripper. The gripper is operated by a wire-based mechanism that extends through a channel 26 in the center of the capstan 23.

Figure 3:
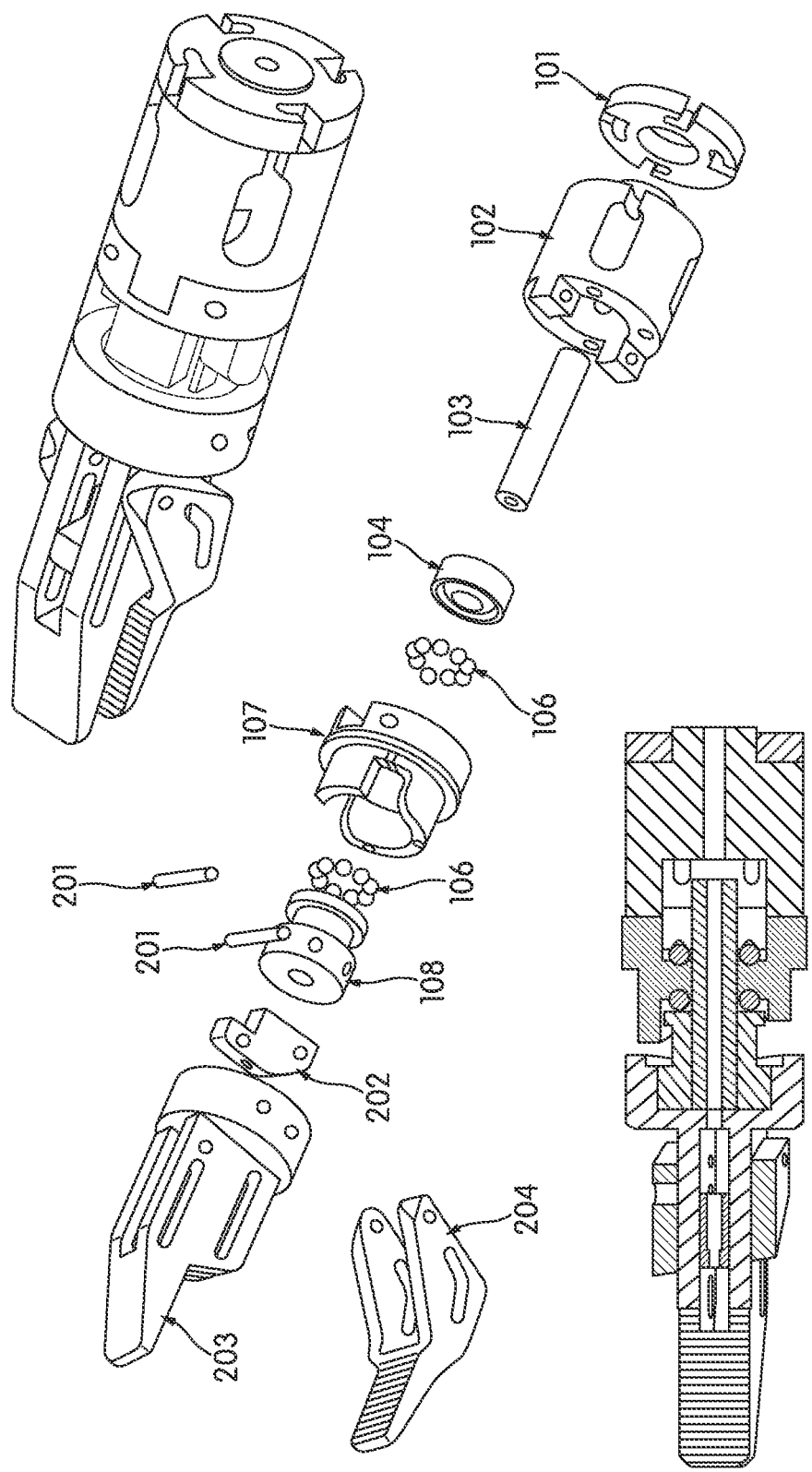
FIG. 3 is a exploded, perspective, and cross-sectional view of a rotatable gripper wrist according to a third embodiment.

FIG. 3 illustrates another example of a rotating wrist assembly. This assembly has two main sub-assemblies: the wrist and the gripper. The wrist base 102 allows the wrist and gripper to be selectively detached from the shaft (e.g., the snake arm) of the continuum robot and also serves as the end disk of a multi-backbone continuum snake robot. The lock nut 101 serves as a means of locking the wrist assembly to the secondary backbones of the snake arm. The hollow screw shaft 103 is threaded into the wrist capstan 108 and is glued to it or attached by press-fit. This screw shaft serves as the shaft hub locking the rotatable wrist capstan 108 to the wrist hub 107. Once the capstan 108 and the screw shaft 103 are connected they are inserted into a bearing made of the wrist capstan 108, the bearing balls 106, the wrist hub 107, and then locked by the lower bearing brace/lock nut 104. The wrist hub 107 is coupled to the wrist base 102 using shear pins.

The gripper includes a fixed jaw 203, a moving jaw 204, a sliding block 202, and a guiding pin. The gripper attaches to the rotating wrist capstan 108 using shear pins 201. Actuation of the gripper is achieved using a superelastic NiTi wire that pushes the sliding block 202, which in turn rotates the moving jaw using a shear pin that passes in the slot openings in the fixed and moving jaws.

The example of FIG. 3 differs from the example of FIG. 2 in that the pulleys are replaced by a wrist hub 107 with sliding surfaces to guide the flexible wire. Also, the example of FIG. 3 eliminates the positive locking terminal. As such, the flexible wire loop can be extended and refracted further linearly through the shaft of the continuum robot and the rotation of the wrist is not limited by a physical structure on the wire. Another difference is that the design in FIG. 3 allows detaching the wrist from the backbones of the snake segment. The end disk of the snake segment, which serves as the wrist hub 102 includes a series of linear grooves allowing for the side insertion of the NiTi backbones of the snake robot. The backbones have enlarged features at their tip that match the grooves in 102. A rotation of lock disk 101 selectively locks the backbones into the wrist hub 102. This selective locking functionality allows for easy replacement of wrist modules.

Figure 4A:
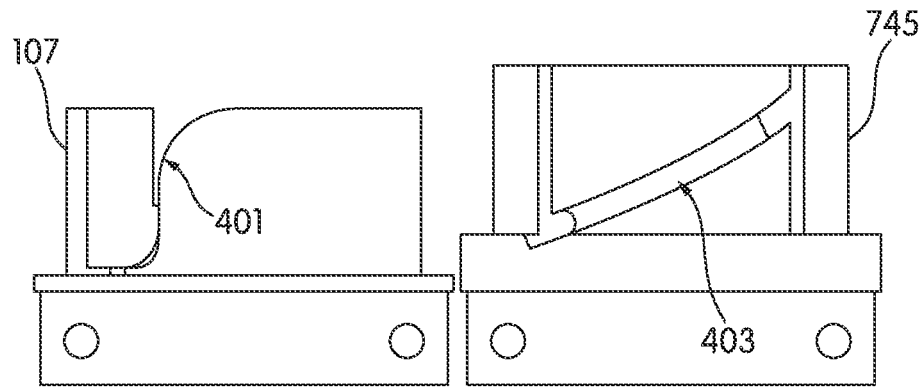
FIGS. 4A and 4B are detailed views of two examples of wrist hub components used with a rotatable gripper wrist.
Figure 4B:
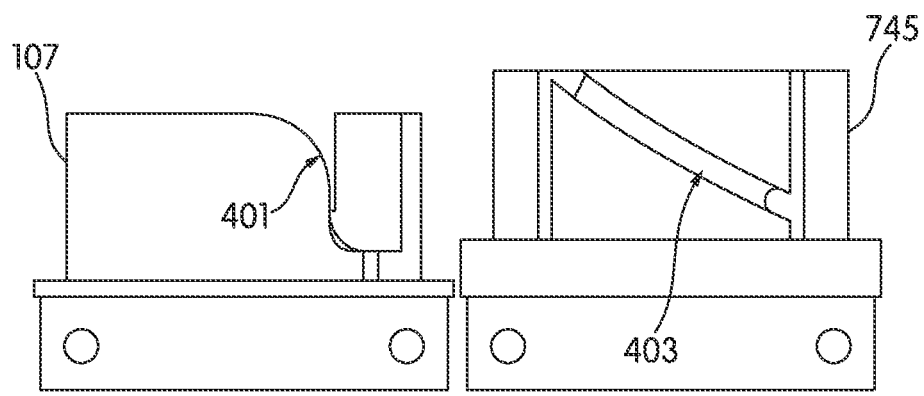

FIG. 4A illustrates the wrist hub 107 in further detail. The wrist hub 107 includes an extrusion 401 that guides the flexible wire and pushes it against the surface of the rotating capstan 108. FIG. 4B shows the wrist hub 107 from a different perspective.

Figure 5:
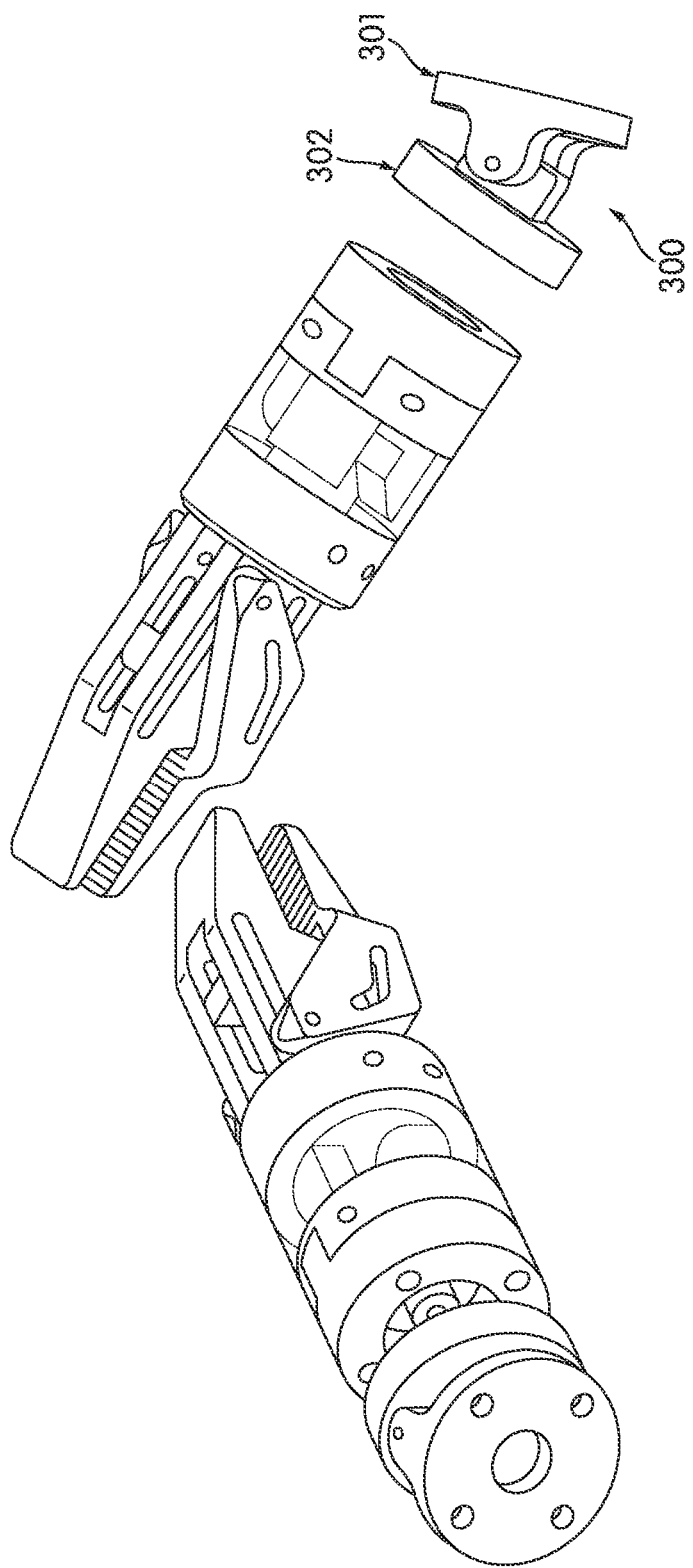
FIG. 5 is a perspective view of a wrist and gripper assembly with a pivot (pitch) joint.

FIG. 5 illustrates a pivot joint 300 that can be included to provide an additional degree of freedom to the rotatable gripper of FIG. 3. The added capability is achieved using a revolute joint assembly including a base 301 and an output link 302 pivotably connected via a pin. There are at least four holes through the base link that provide access for superelastic NiTi wires that control the rotatable gripper assembly. In one example, two adjacent holes are used to pass either end of the flexible wire loop used to actuate the rotatable wrist and the other two holes are used to actuate the revolute joint using push-pull actuation through a wire rope connected to the output link 302. In another embodiment, the revolute joint is actuated through superelastic NiTi tubes connected to the output link 302 and passing through guide tubes in the base 301 and the wrist is actuated through wire ropes that pass through the NiTi tubes of the revolute joint.

Figure 6:
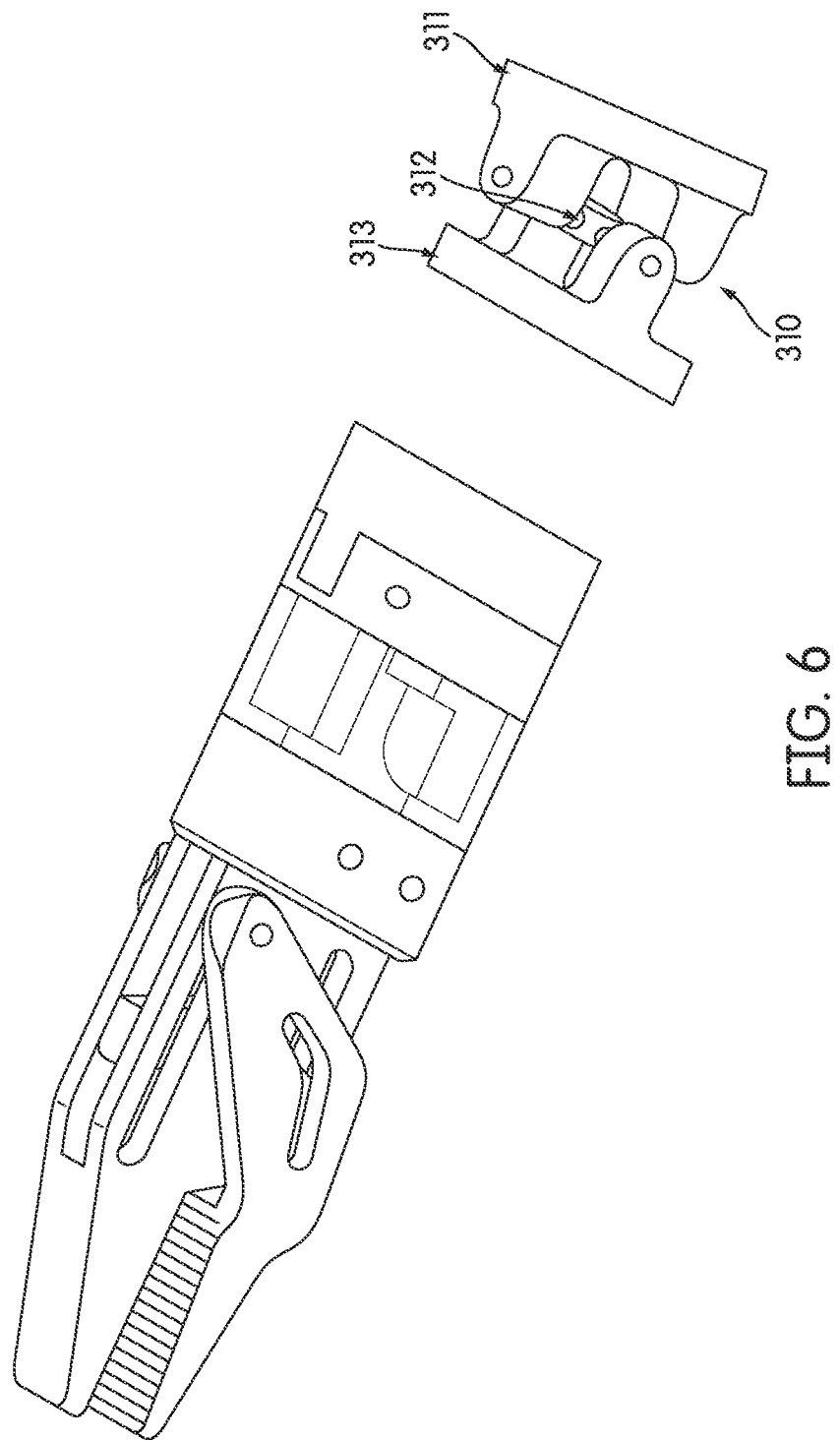
FIG. 6 is a perspective view of a wrist and gripper assembly with a gimbal (yaw and pitch) joint.

FIG. 6 illustrates an alternative joint assembly 310 for connecting the rotatable gripper to the shaft of the continuum robot. This example provides yet another degree of freedom (both yaw and pitch) in addition to the rotating capabilities. The added degree of freedom is achieved using a Cardan (Hooke) joint assembly. The joint assembly includes a base 311, a gimbal 312, and an output link 313. The gimbal is connected to the base and output links via pins. The base link again has at least four holes. In one example, two opposing holes are used to pass the actuation wires of the yaw degree of freedom while the other two holes are used to pass actuation wires of the pitch direction. The wrist actuation in a design using only four holes in the base 311 would require the use of a rotation tube and a gripper as illustrated in FIG. 1. In another embodiment, the base 311 has at least six holes and an additional center hole for actuating the gripper. Two holes are used to pass wires for actuating the pitch axis, two for actuating the yaw, and two to actuate the rotation of the gripper. In such constructions, a hole must also be provided through the center of gimbal 312 to allow the mechanism for actuating the gripper to pass through the joint 310. In some other constructions, gimbal 312 is replaced with a binary link having two axially offset pivots that are mutually perpendicular.

Figure 7:
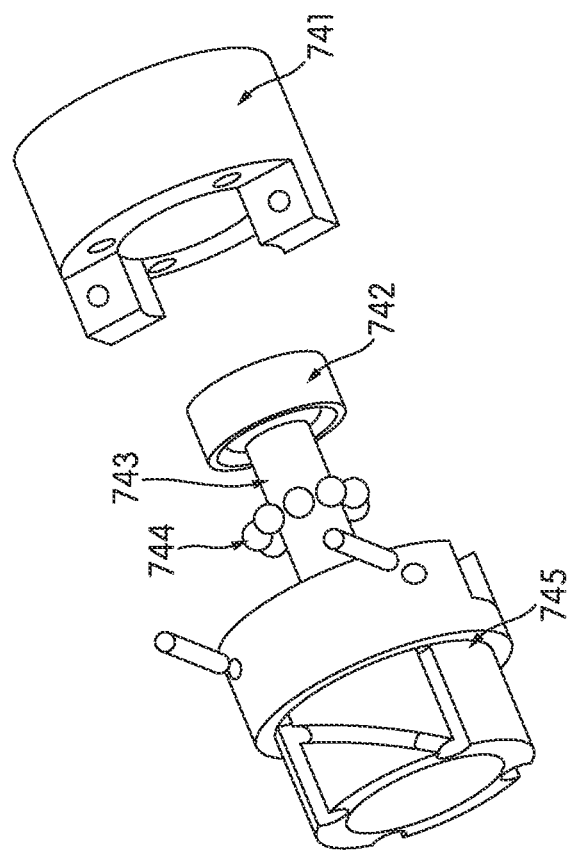
FIG. 7 is an exploded with of a rotatable gripper wrist according to a fourth embodiment.
Figure 7:
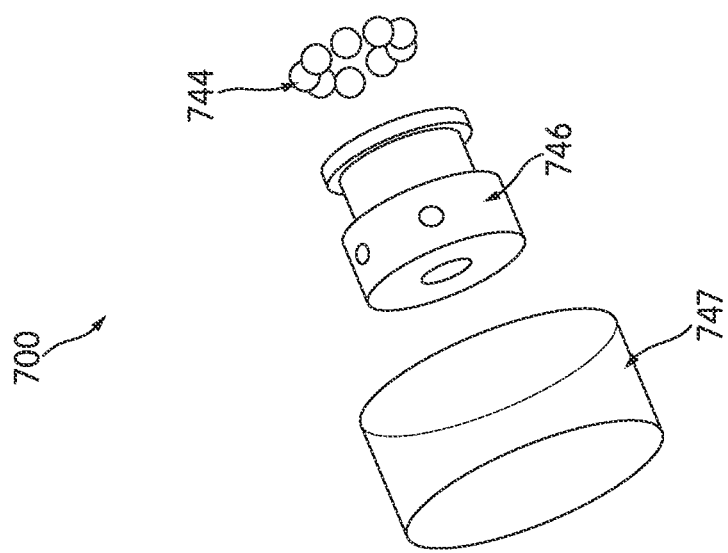

FIG. 7 illustrates another alternative rotatable wrist 700 for a gripper assembly. The wrist includes a snake end disk 741, a bearing nut 742, a vented screw 743, bearing balls 744, a wrist hub 745, a capstan 746, and a cover ring 747. When connected to the capstan assembly 746, the bearing nut 742 supports the bottom set of bearing balls 744 and locks the entire wrist structure around the wrist hub 745. The capstan 746 has locating pins for mounting the gripper jaw.

FIGS. 4A and 4B further illustrate the differences between the wrist hub 107 of the example of FIG. 3 and the wrist hub B45 of the example of FIG. 7. Wrist hub 107 includes two smooth extrusions 401 to allow routing of the wire rope loop that is used to control the rotation of the capstan and, thereby, the gripper. Wrist hub 745 includes a groove 403 that routes the wire rope to the correct position to wrap around the capstan 746. As the wire rope is inserted or retracted from the shaft of the continuum robot to control the rotation of the wrist, the wire rope move linearly through the grooves of the wrist hub 745.

Figure 8C:
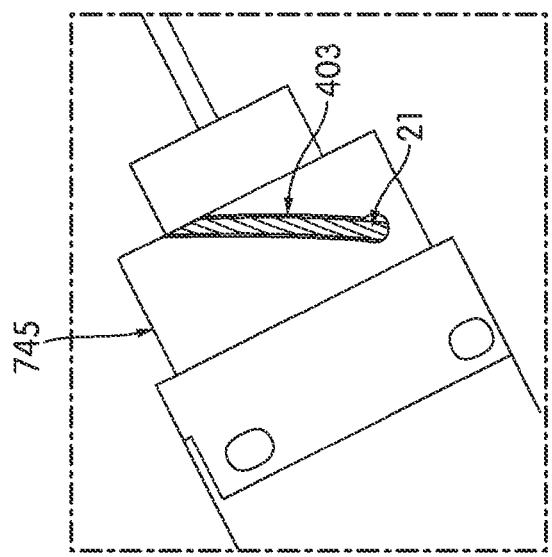
FIG. 8C is a side view of the assembled rotatable gripper wrist of FIG. 7 fitted with the flexible control wire.
Figure 8B:
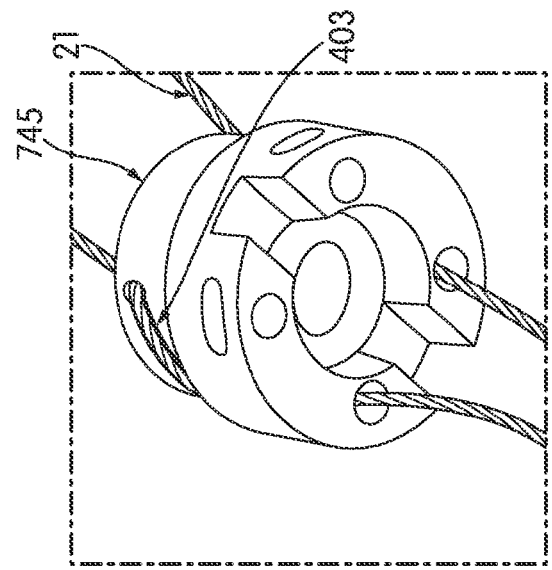
FIG. 8B is a perspective view of the bottom of the wrist hub of FIG. 8A.
Figure 8A:
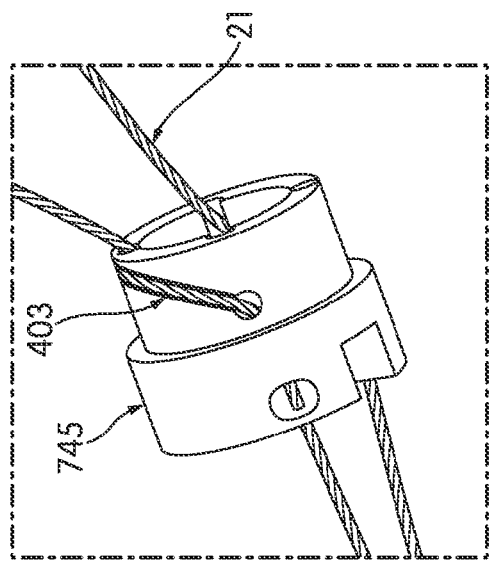
FIG. 8A is a side view of the wrist hub component of the rotatable gripper wrist of FIG. 7 fitted with a flexible control wire.

FIGS. 8A, 8B, and 8C show various components of the wrist assembly of FIG. 7 fitted with a flexible wire loop. FIG. 8A shows the wrist hub 745 from the side and illustrates the ends of the wire loop running through the grooves 403 of the wrist hub 745 and extending out of the bottom of the wrist hub 745. FIG. 8B shows the same assembly from the bottom. In FIG. 8C, the entire rotatable wrist assembly is assembled and attached to the distal end of a continuum robot. The wire loop is visible in the groove 403 of the wrist hub B75 in FIG. 8C.

Thus, the invention provides, among other things, a rotatable wrist assembly for an articulable gripper tool. Various features and advantages of the invention are set forth in the following claims.

What is claimed is:

1. A continuum robot comprising:
   a plurality of adjustable segments along a shaft of the continuum robot;
   a gripper selectively connectable to a distal end of the shaft;
   a rotatable wrist connecting the gripper to the distal end of the shaft, the rotatable wrist including
      a wrist hub, the wrist hub being non-rotatably connected to the distal end of the shaft,
      a wrist capstan rotatably connected to the wrist hub and non-rotatably connected to the gripper, and
      a flexible wire loop extending through the wrist hub and partially contacting the wrist capstan, wherein linear movement of the flexible wire loop through the shaft causes rotation of the wrist capstan due to friction between the flexible wire loop and the wrist capstan,
   wherein the wrist hub includes a first groove and a second groove, wherein the first groove is positioned at an angle relative to the shaft of the continuum robot, and wherein a first end of the flexible wire loop is positioned within the first groove such that the first groove guides linear movement of the first end of the flexible loop.

2. The continuum robot of claim 1, wherein the wrist capstan includes a grooved surface, and the flexible wire loop includes a spherical terminal that contacts the grooved surface of the wrist capstan.

3. The continuum robot of claim 1, wherein the second groove is positioned at an angle relative to the shaft of the continuum robot, and wherein a second end of the flexible wire loop is positioned within the second groove such that the second groove guides the linear movement of the second end of the flexible loop.

4. The continuum robot of claim 3, wherein a portion of the flexible wire loop extends from the first groove to the second groove and contacts the wrist capstan such that linear movement of the portion of the flexible wire loop that extends from the first groove to the second groove cause rotation of the wrist capstan.

5. The continuum robot of claim 1, further comprising a pivot joint connecting the rotatable wrist to the shaft of the continuum robot, wherein the pivot joint controllably adjusts an angle of the gripper relative to the shaft of the continuum robot.

6. The continuum robot of claim 1, further comprising a universal joint connecting the rotatable wrist to the shaft of the continuum robot, wherein the universal joint controllably adjusts yaw and pitch angles of the gripper relative to the shaft of the continuum robot and the wrist controls roll of the gripper.

7. The continuum robot of claim 1, further comprising an actuation channel extending through a center of the wrist capstan, wherein actuation of the gripper is controlled by at least one wire extending through the actuation channel.

8. The continuum robot of claim 1, further comprising a locking component for selectively attaching the rotatable wrist to the shaft of the continuum robot.

9. A rotatable wrist for placement and manipulation of an actuatable medical device, the rotatable wrist comprising:
   a wrist hub, the wrist hub being non-rotatably coupled to a distal end of a positioning device, wherein the positioning device includes a continuum robot with a plurality of adjustable segments along a shaft of the continuum robot;
   a wrist capstan rotatably connected to the wrist hub and non-rotatably connected to the actuatable medical device; and
   a flexible wire loop extending through the wrist hub and partially contacting the wrist capstan, wherein linear movement of the flexible wire loop through the positioning device causes rotation of the wrist capstan due to friction between the flexible wire loop and the wrist capstan,
   wherein the wrist hub includes a first groove and a second groove, wherein the first groove is positioned at an angle relative to the shaft of the continuum robot, and wherein a first end of the flexible wire loop is positioned within the first groove such that the first groove guides linear movement of the first end of the flexible loop.

10. The rotatable wrist of claim 9, wherein the actuatable medical device includes a gripper.

11. The rotatable wrist of claim 9, wherein the positioning device includes a positioning shaft for controlling a position of the actuatable medical device in a body cavity during minimally invasive surgical procedures.

12. The rotatable wrist of claim 9, wherein the wrist capstan includes a grooved surface, and the flexible wire loop includes a spherical terminal that contacts the grooved surface of the wrist capstan.

13. The rotatable wrist of claim 9, wherein the second groove is positioned at an angle relative to the shaft of the continuum robot, and wherein a second end of the flexible wire loop is positioned within the second groove such that the second groove guides the linear movement of the second end of the flexible loop.

14. The rotatable wrist of claim 13, wherein a portion of the flexible wire loop extends from the first groove to the second groove and contacts the wrist capstan such that linear movement of the portion of the flexible wire loop that extends from the first groove to the second groove cause rotation of the wrist capstan.

15. The rotatable wrist of claim 9, further comprising a pivot joint connecting the rotatable wrist to the positioning device, wherein the pivot joint controllably adjusts an angle of the actuatable medical device relative to the positioning device.

16. The rotatable wrist of claim 9, further comprising a universal joint connecting the rotatable wrist to the positioning device, wherein the universal joint controllably adjusts yaw and pitch angles of the actuatable medical device relative to the positioning device and the wrist controls roll of the actuatable medical device.

17. The rotatable wrist of claim 9, further comprising an actuation channel extending through a center of the wrist capstan, wherein actuation of the actuatable medical device is controlled by at least one wire extending through the actuation channel.

18. The rotatable wrist of claim 9, further comprising a locking component for selectively attaching the rotatable wrist to the positioning device.

* * * * *